(12) United States Patent
Yoshioka

(10) Patent No.: US 11,717,220 B2
(45) Date of Patent: Aug. 8, 2023

(54) SHEET FOR BIOSENSOR

(71) Applicant: NITTO DENKO CORPORATION, Ibaraki (JP)

(72) Inventor: Ryoma Yoshioka, Ibaraki (JP)

(73) Assignee: NITTO DENKO CORPORATION, Ibaraki (JP)

(*) Notice: Subject to any disclaimer, the term of this patent is extended or adjusted under 35 U.S.C. 154(b) by 594 days.

(21) Appl. No.: 16/608,108

(22) PCT Filed: Jan. 26, 2018

(86) PCT No.: PCT/JP2018/002519
§ 371 (c)(1),
(2) Date: Oct. 24, 2019

(87) PCT Pub. No.: WO2018/198456
PCT Pub. Date: Nov. 1, 2018

(65) Prior Publication Data
US 2020/0093439 A1   Mar. 26, 2020

(30) Foreign Application Priority Data

Apr. 28, 2017 (JP) ................................. 2017-090540

(51) Int. Cl.
*A61B 5/00* (2006.01)
*A61B 5/25* (2021.01)
(Continued)

(52) U.S. Cl.
CPC .............. *A61B 5/6833* (2013.01); *A61B 5/25* (2021.01); *A61B 5/01* (2013.01); *A61B 5/0245* (2013.01);
(Continued)

(58) Field of Classification Search
CPC ..... A61B 5/01; A61B 5/02141; A61B 5/0245; A61B 5/05; A61B 5/14532; A61B 5/25;
(Continued)

(56) References Cited

U.S. PATENT DOCUMENTS 4,852,571 A    8/1989  Gadsby et al.
5,352,315 A    10/1994 Carrier et al.
(Continued)

FOREIGN PATENT DOCUMENTS

CN    101303347 A    11/2008
CN    102614047 A    8/2012
(Continued)

OTHER PUBLICATIONS

Office Action issued for corresponding Taiwanese Patent Application No. 107104936 dated May 5, 2021, along with an English translation.
(Continued)

*Primary Examiner* — Orlando Bousono
(74) *Attorney, Agent, or Firm* — Hauptman Ham, LLP

(57) ABSTRACT

A biosensor sheet includes a pressure-sensitive adhesive layer for attaching to a surface of a living body, and a probe disposed on the pressure-sensitive adhesive layer, wherein the probe has an exposure region in which the pressure-sensitive adhesive layer is exposed.

7 Claims, 11 Drawing Sheets

(51) Int. Cl.
  *A61B 5/01* (2006.01)
  *A61B 5/021* (2006.01)
  *A61B 5/0245* (2006.01)
  *A61B 5/291* (2021.01)
  *A61B 5/296* (2021.01)

(52) U.S. Cl.
  CPC ........... *A61B 5/02141* (2013.01); *A61B 5/291* (2021.01); *A61B 5/296* (2021.01)

(58) Field of Classification Search
  CPC ......... A61B 5/257; A61B 5/291; A61B 5/296; A61B 5/6833; G01R 3/00; G01R 1/073; G01R 1/0735; G06F 3/041; G06F 3/044; G06F 3/0445; G06F 3/0446; G06F 2203/04103; G06F 2203/04112; H01L 22/00; G01N 27/3272
  See application file for complete search history.

(56) References Cited

U.S. PATENT DOCUMENTS

| | | | |
|---|---|---|---|
| 9,274,060 B1* | 3/2016 | Ascheman | G01N 21/6408 |
| 2007/0000776 A1* | 1/2007 | Karube | G01N 27/3272 |
| | | | 204/403.01 |
| 2007/0043304 A1* | 2/2007 | Katayama | A61B 5/411 |
| | | | 128/903 |
| 2012/0129268 A1* | 5/2012 | Mayer | G01N 21/77 |
| | | | 156/60 |
| 2012/0189796 A1 | 7/2012 | Aoyagi et al. | |
| 2013/0018249 A1 | 1/2013 | Storm | |
| 2014/0034847 A1* | 2/2014 | Mayer | G01N 21/643 |
| | | | 250/459.1 |
| 2015/0177154 A1* | 6/2015 | Papkovsky | G01N 31/22 |
| | | | 436/164 |
| 2015/0335288 A1 | 11/2015 | Toth et al. | |
| 2016/0363491 A1* | 12/2016 | Iwase | G01L 5/00 |
| 2017/0258357 A1 | 9/2017 | Riemenschneider et al. | |
| 2018/0199443 A1 | 7/2018 | Okumura et al. | |
| 2022/0110559 A1* | 4/2022 | Frick | A61B 5/14532 |

FOREIGN PATENT DOCUMENTS

| | | |
|---|---|---|
| JP | 2011-30678 A | 2/2011 |
| JP | 2012-10978 A | 1/2012 |
| JP | 2013-523313 A | 6/2013 |
| JP | 2015-123198 A | 7/2015 |
| JP | 2016-364 A | 1/2016 |
| JP | 2017-22236 A | 1/2017 |
| WO | 02/28279 A1 | 4/2002 |
| WO | 2015/188937 A1 | 12/2015 |
| WO | 2018/004614 A1 | 1/2018 |

OTHER PUBLICATIONS

The Extended European Search Report issued for corresponding European Patent Application No. 18792282.8 dated Oct. 13, 2020.
Yeo et al. "Multifunctional Epidermal Electronics Printed Directly Onto the Skin", Advanced Materials, 2013, vol. 25, p. 2773-2778, Wiley-VCH Verlag GmbH & Co, Weinheim.
International Search Report for corresponding international application PCT/JP2018/002519 dated Apr. 24, 2018.
Chang-Hsiu Chen et al. "Mechanical characterizations of cast Poly (3,4-ethylenedioxythiophene):Poly (styrenesulfonate)/Polyvinyl Alcohol thin films", Synthetic Metals 161, 2011, pp. 2259-2267.
Office Action issued for corresponding Japanese Patent Application No. 2017-090540 dated Sep. 29, 2020, along with an English machine translation.
Office Action dated Nov. 23, 2021 for corresponding Chinese Patent Application No. 201880027336.3, along with an English translation.
Office Action dated May 16, 2022 for corresponding Chinese Patent Application No. 201880027336.3, along with an English machine translation.
Office Action dated Jun. 13, 2022 for corresponding Indian Patent Application No. 201917042152.
Examination Report No. 1 dated Mar. 6, 2023 for corresponding Australian Patent Application No. 2018259567 (5 pages).
Communication pursuant to Article 94(3) EPC dated Jan. 11, 2023 for corresponding European Patent Application No. 18 792 282.8 (5 pages).

\* cited by examiner

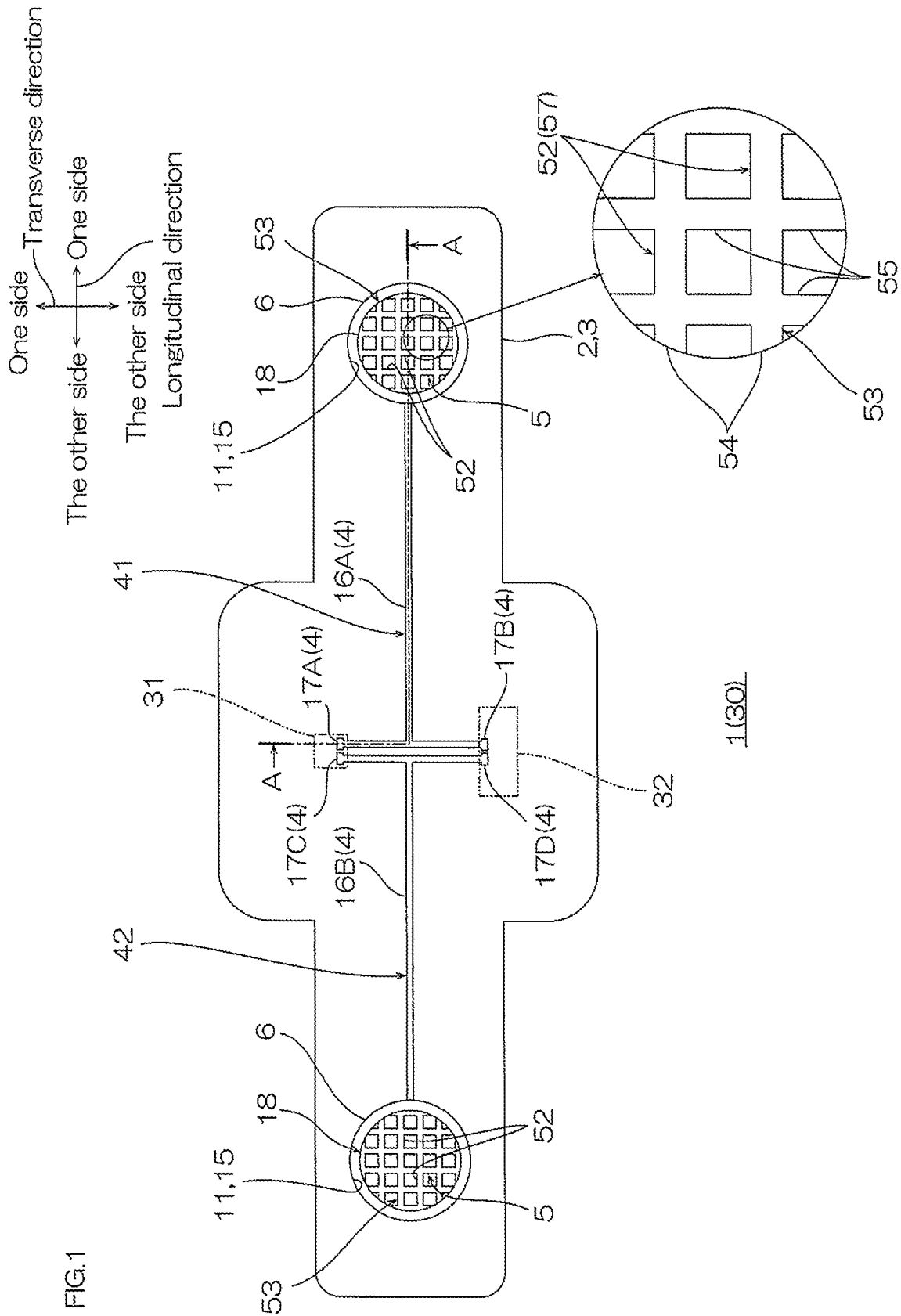

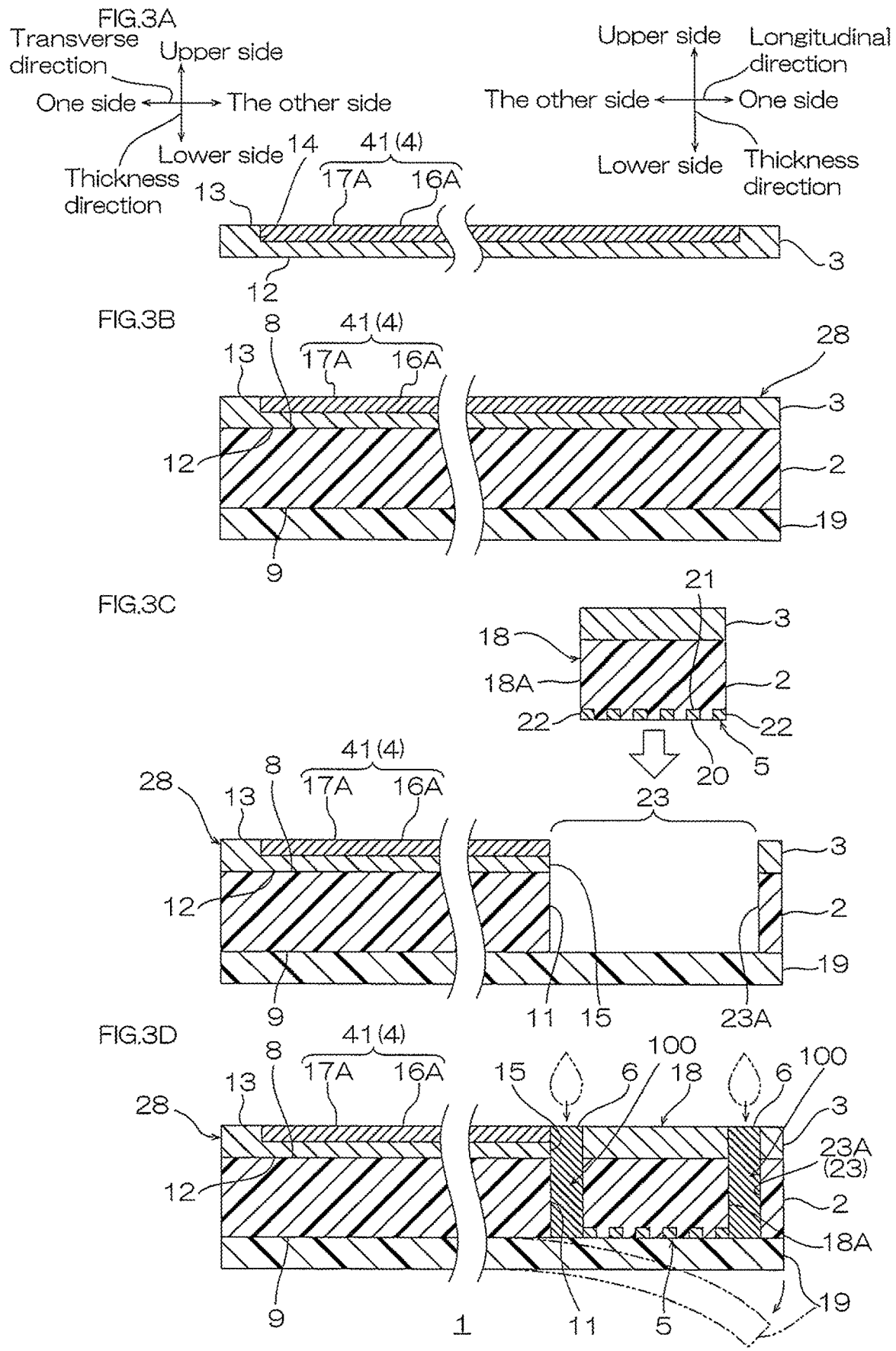

Upper side
↕
Lower side

FIG.5
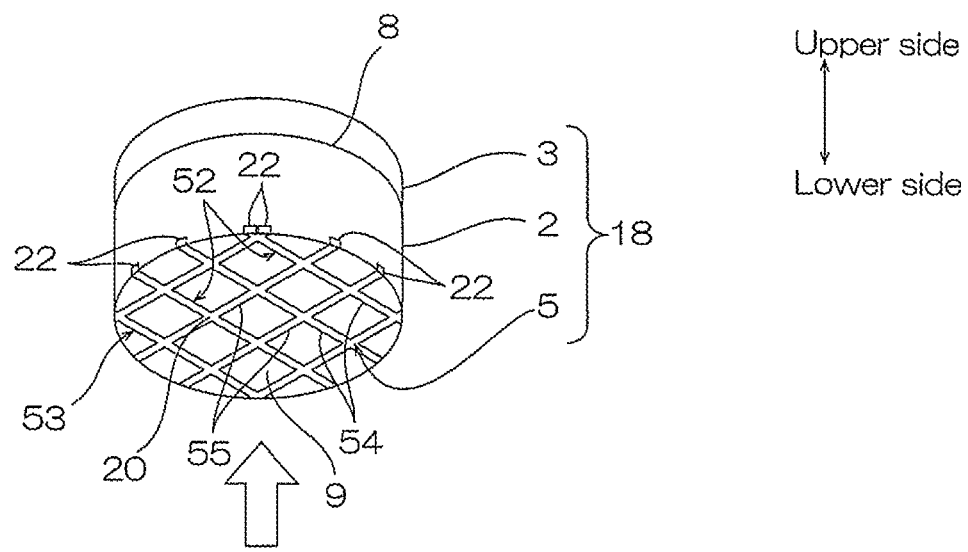
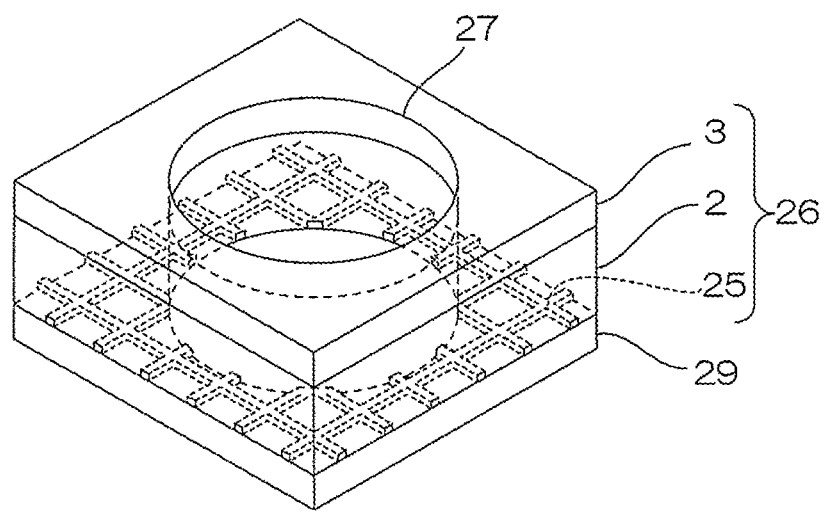

SHEET FOR BIOSENSOR

CROSS REFERENCE TO RELATED APPLICATION

This application claims the priority of Japanese Patent Application No. 2017-090540, filed on Apr. 28, 2017, in the JPO (Japanese Patent Office). Further, this application is the National Phase Application of International Application No. PCT/JP2018/002519, filed on Jan. 26, 2018, which designates the United States and was published in Japan. Both of the priority documents are hereby incorporated by reference in their entireties.

TECHNICAL FIELD

The present invention relates to a sheet for biosensor (biosensor sheet).

BACKGROUND ART

Conventionally, a biosensor that is used by attaching it to the human skin and that detects biosignals has been known.

For example, Patent Document 1 has proposed a biocompatible polymer substrate including a data input module, adhesive polymer layer, disc shape electrode disposed on the polymer layer, and wires connecting the data input module and electrode (ref: Patent Document 1).

In such a biocompatible polymer substrate, the polymer layer is attached to the human skin, the electrode detects the biosignals, for example, voltage signals based on the heart muscles, and the data input module receives and records the voltage signals based on the heart muscles.

CITATION LIST

Patent Document

Patent Document 1: Japanese Unexamined Patent Publication No. 2012-10978

SUMMARY OF THE INVENTION

Problem to be Solved by the Invention

However, in the biocompatible polymer substrate described in Patent Document 1, as shown in FIG. 2B, because the electrode 51 has a disc shape, when the polymer layer is attached to the human skin 33 and the electrode 51 is made into contact with the skin 33, the electrode 51 may not be able to conform to the subtle bumps and dips of the skin 33. In such a case, the subtle bumps and dips cause gaps 34 between the electrode 51 and the surface of the skin 33. Therefore, with the biocompatible polymer substrate described in Patent Document 1, improvement in biosignal sensing precision is limited.

Thus, the present invention provides a biosensor sheet with which a probe can conform to subtle bumps and dips on the surface of the living body.

Means for Solving the Problem

The present invention [1] includes a biosensor sheet including a pressure-sensitive adhesive layer for attaching to a surface of a living body and a probe disposed on the pressure-sensitive adhesive layer, wherein the probe has an exposure region in which the pressure-sensitive adhesive layer is exposed.

With such a configuration, the probe has the exposure region in which the pressure-sensitive adhesive layer is exposed, and therefore when the pressure-sensitive adhesive layer is attached to a surface of a living body to allow the one side of the probe to make contact with the surface of the living body, exposure region allows the probe to bend so as to follow the surface of the living body, and the probe can conform to the subtle bumps and dips on the surface of the living body. Therefore, precision on sensing of the biosignal can be improved in the biosensor including a biosensor sheet.

The present invention [2] includes the biosensor sheet described in [1] above, wherein the probe has a thin layer shape.

With such a configuration, the probe has a thin layer shape, and therefore the user's discomfort in wearing can be decreased when the biosensor sheet is attached to the surface of the living body.

The present invention [3] includes the biosensor sheet described in [1] or [2] above, wherein the exposure region includes a plurality of holes disposed in spaced apart relation.

With such a configuration, because the exposure region includes a plurality of holes disposed in spaced apart relation, while giving flexibility to the probe, rigidity of the probe can be ensured.

The present invention [4] includes the biosensor sheet described in [3] above, wherein the probe includes a bar portion that defines the plurality of holes.

With such a configuration, the plurality of holes are defined by the bar portion, and therefore the plurality of holes can be disposed regularly, and flexibility can be given to the probe reliably. Therefore, the probe can be reliably allowed to conform to the subtle bumps and dips on the surface of the living body.

The present invention [5] includes the biosensor sheet described in [4] above, wherein the bar portion has a lattice shape.

With such a configuration, the plurality of holes are defined by the bar portion having a lattice shape, and therefore the plurality of holes can be homogenously disposed in good balance in the entire probe. Therefore, the entire probe can be allowed to conform to the subtle bumps and dips of the surface of the living body.

The present invention [6] includes biosensor sheet described in [4] or [5] above, wherein the bar portion includes a plurality of first bar portions extending in a direction orthogonal to the thickness direction of the pressure-sensitive adhesive layer so as to be parallel to each other with a space provided therebetween, and a plurality of second bar portions that bridge adjacent first bar portions of the plurality of first bar portions.

With such a configuration, the plurality of holes are defined by a plurality of first bar portion parallel to each other with a space provided therebetween, and a plurality of second bar portions bridge the first bar portions adjacent to each other, while giving flexibility to the probe, rigidity can be kept by the second bar portion. Furthermore, even if the bar portion is partially broken, the first bar portion is bridged by the second bar portion and therefore conductivity can be ensured, and therefore there are advantages such as keeping the functions of the sensor in the biosensor including a biosensor sheet.

The present invention [7] includes the biosensor sheet described in [6] above, wherein the plurality of first bar portions extend in a first direction orthogonal to the thickness direction; the plurality of second bar portions extend in a second direction crossing both directions of the thickness direction and the first direction so as to be spaced apart from each other and to cross the plurality of first bar portions; the size of the first bar portion in the second direction: the size of the hole in the second direction is 5:95 to 50:50; and the size of the second bar portion in the first direction: the size of the hole in the first direction is 5:95 to 50:50.

With such a configuration, the size of the first bar portion in the second direction: the size of the hole in the second direction is the above-described range, and the size of the second bar portion in the first direction: the size of the hole in the first direction is the above-described range, and ratio of the area of the bar portion to the area of the holes can be ensured in good balance, and the probe can conform to subtle bumps and dips of the surface of the living body even more reliably.

The present invention [8] includes the biosensor sheet described in [7] above, wherein the size of the first bar portion in the second direction, and the size of the second bar portion in the first direction are 10 μm or more and 500 μm or less; and the size of the hole in the first direction, and the size of the hole in the second direction are 50 μm or more and 1000 μm or less.

With such a configuration, the size of the first bar portion in the second direction and the size of the second bar portion in the first direction are within the above-described range, and the size of the hole in the first direction and the size of the hole in the second direction are within the above-described range, and therefore the ratio of the area of the bar portion to the area of the holes can be ensured even more in good balance.

Effects of the Invention

With the biosensor sheet of the present invention, the probe can conform to the subtle bumps and dips on the surface of the living body.

BRIEF DESCRIPTION OF THE DRAWINGS

FIG. 1 shows a plan view of a biosensor laminate (laminate for biosensor) as an embodiment of the biosensor sheet of the present invention.

FIG. 3A to FIG. 3D are process diagrams illustrating production of the biosensor laminate shown in FIG. 1, FIG. 3A illustrating a step of preparing a substrate and a wire layer, FIG. 3B illustrating a step of bonding the pressure-sensitive adhesive layer with the substrate, FIG. 3C illustrating a step of forming a through hole and allowing a probe member to fit, and FIG. 3D illustrating a step of forming a connector.

FIG. 5 shows perspective views illustrating production processes of a probe member.

DESCRIPTION OF THE EMBODIMENTS

Embodiment

1. Schematic Configuration of Biosensor Laminate

A biosensor laminate 1 as an embodiment of the biosensor sheet of the present invention is described with reference to FIG. 1 to FIG. 5.

In FIG. 1, left-right direction on the sheet is longitudinal direction (first direction) of the biosensor laminate 1. Right side on the sheet is longitudinal one side (one side in first direction), left side on the sheet is longitudinal other side (the other side in first direction).

In FIG. 1, up-down direction on the sheet is transverse direction (direction orthogonal to longitudinal direction, width direction, and second direction orthogonal to (crossing) first direction) of the biosensor laminate 1. Upper side on the sheet is one side in transverse direction (one side in width direction, one side in second direction), and lower side on the sheet is the other side in transverse direction (the other side in width direction, the other side in second direction).

In FIG. 1, paper thickness direction on the sheet is up-down direction (thickness direction, third direction orthogonal to first direction and second direction) of the biosensor laminate 1. Near side on the sheet is upper side (one side in thickness direction, one side in third direction), and far side on the sheet is lower side (the other side in thickness direction, the other side in third direction).

The directions are in accordance with the direction arrows described in the figures.

These definitions of the directions are not intended to limit the orientations of the biosensor laminate 1 and wearable electrocardiograph 30 (described later) at the time of production and use.

Figure 2A:
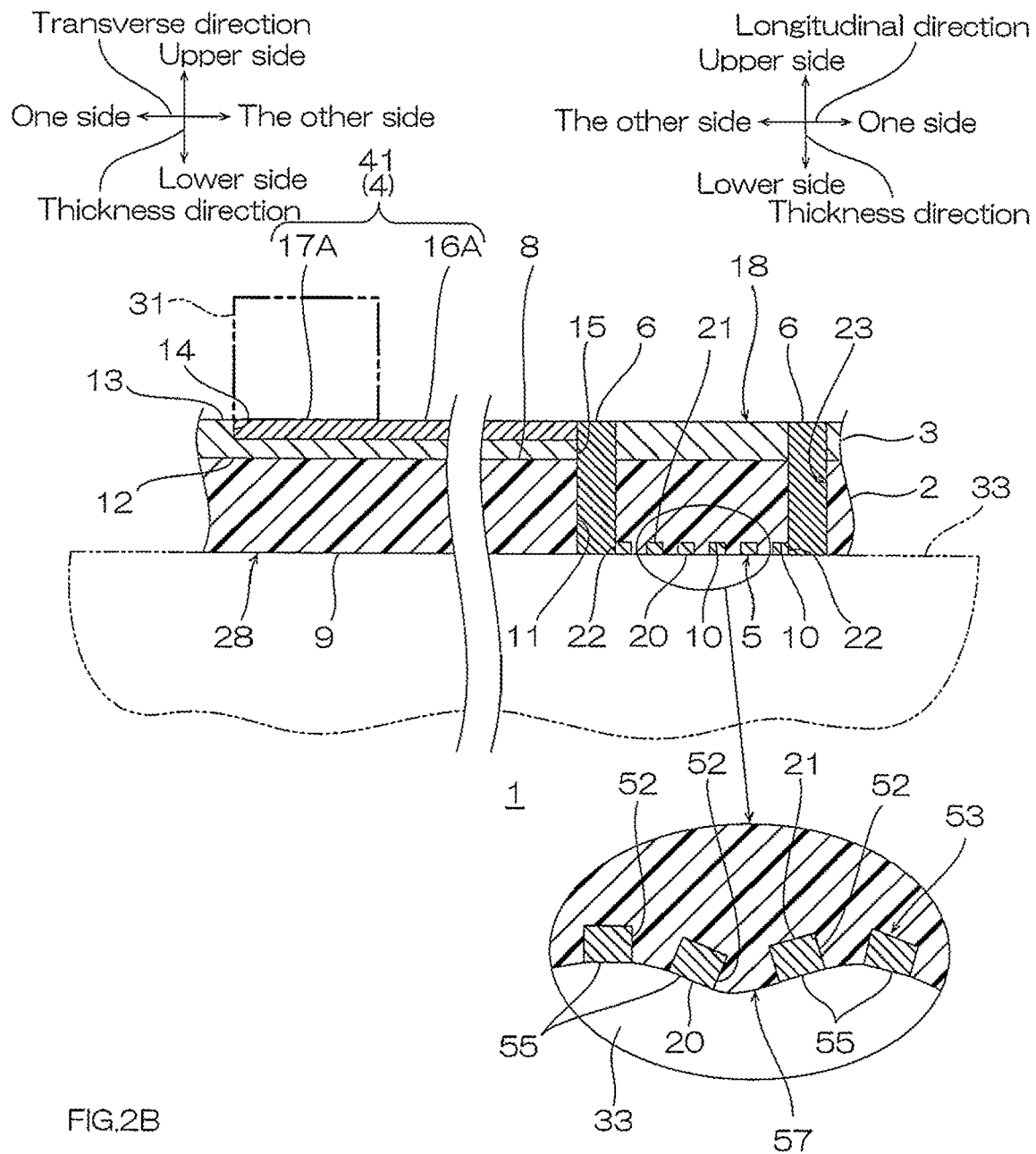
FIG. 2A is a cross sectional view along line A-A of the biosensor laminate shown in FIG. 1.
Figure 2B:
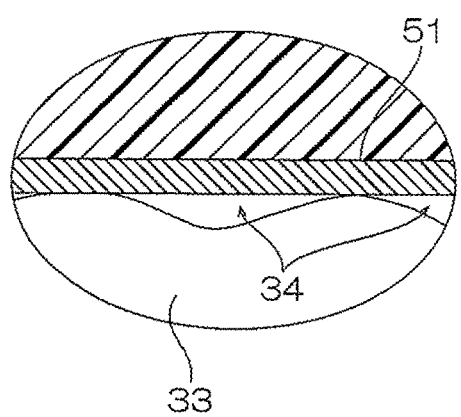
FIG. 2B illustrates a prior art, in which the probe has a plate shape.

As shown in FIG. 1 to FIG. 2A, the biosensor laminate 1 has a substantially flat plate shape extending in longitudinal direction. The biosensor laminate 1 includes a pressure-sensitive adhesive layer 2 for attaching to the surface of the living body, a substrate 3 disposed on the upper face of the pressure-sensitive adhesive layer 2, a wire layer 4 disposed on the substrate 3, a probe 5 disposed on the pressure-sensitive adhesive layer 2, and a connecter 6 that electrically connects the wire layer 4 with the probe 5. In FIG. 1, for convenience, the pressure-sensitive adhesive layer 2 and the substrate 3 overlapping with the probe 5 in up-down direction are omitted.

The pressure-sensitive adhesive layer 2 forms the lower face of the biosensor laminate 1. The pressure-sensitive adhesive layer 2 is a layer that gives pressure-sensitive adhesiveness to the lower face of the biosensor laminate 1 for attaching the lower face of the biosensor laminate 1 to the surface of the living body (skin 33, etc.). The pressure-sensitive adhesive layer 2 forms the outline shape of the biosensor laminate 1. The pressure-sensitive adhesive layer 2 has, for example, a flat plate shape extending in longitudinal direction. To be specific, the pressure-sensitive adhesive layer 2 may have a band shape extending in longitudinal direction, with a longitudinal center portion bulging toward transverse both outsides. In the pressure-sensitive adhesive layer 2, both end edges in transverse direction of the longitudinal center portion are positioned at transverse both outsides relative to the both end edges in transverse direction of other than the longitudinal center portion.

The pressure-sensitive adhesive layer 2 has an adhesive upper face 8 and an adhesive lower face 9. The adhesive upper face 8 has a flat face. The adhesive lower face 9 is disposed to face each other at a lower side of the adhesive upper face 8 in spaced apart relation.

The pressure-sensitive adhesive layer 2 has adhesion openings 11 at its longitudinal both ends. Each of the two adhesion openings 11 has a substantially ring shape in plan view. The adhesion opening 11 penetrates the pressure-sensitive adhesive layer 2 in thickness direction. The adhesion opening 11 is filled with the connecter 6.

The adhesion opening 11 inside the adhesive lower face 9 has adhesion grooves 10 in correspondence with the probe 5 (described later). The adhesion groove 10 is opened toward the lower side.

The material of the pressure-sensitive adhesive layer 2 is not particularly limited as long as it has, for example, pressure-sensitive adhesiveness, and preferably, a biocompatible material is used. Examples of such a material include acrylic pressure-sensitive adhesives and silicone pressure-sensitive adhesives, and preferably, acrylic pressure-sensitive adhesives are used. For the acrylic pressure-sensitive adhesive, for example, the one described in Japanese Unexamined Patent Publication No. 2003-342541 in which acrylic polymer is used as a main component is used.

The pressure-sensitive adhesive layer 2 has a thickness of, as a distance between the adhesive upper face 8 and the adhesive lower face 9 in a region other than the adhesion groove 10, for example, 10 μm or more, preferably 20 μm or more, and for example, less than 100 μm, preferably 50 μm or less.

The substrate 3 forms an upper face of the biosensor laminate 1. The substrate 3 forms an outline shape of the biosensor laminate 1 along with the pressure-sensitive adhesive layer 2. The shape in plan view of the substrate 3 is the same as the shape in plan view of the pressure-sensitive adhesive layer 2. The substrate 3 is disposed at the entire upper face of the pressure-sensitive adhesive layer 2 (excluding the region where connecter 6 is provided). The substrate 3 is a support layer supporting the pressure-sensitive adhesive layer 2. The substrate 3 has a flat plate shape extending in longitudinal direction.

The substrate 3 has a substrate lower face 12 and a substrate upper face 13. The substrate lower face 12 has a flat face.

The substrate lower face 12 is in contact with (pressure sensitive adhesion) the adhesive upper face 8 of the pressure-sensitive adhesive layer 2.

The substrate upper face 13 is disposed to face each other at the upper side of the substrate lower face 12 in spaced apart relation. The substrate upper face 13 has a substrate groove 14 in correspondence with the wire layer 4. The substrate groove 14 has the same pattern as that of the wire layer 4 in plan view. The substrate groove 14 is opened toward the upper side.

The substrate 3 has a substrate opening 15 in correspondence with the adhesion opening 11. The substrate opening 15 communicates with the adhesion opening 11 in thickness direction. The substrate opening 15 has a substantially ring shape in plan view with the same shape and the same size as those of the adhesion opening 11.

The material of the substrate 3 has, for example, stretching property. The material of the substrate 3 has, for example, insulating characteristics. For such a material, for example, resin is used. Examples of the resin include thermoplastic resin such as polyurethane resin, silicone resin, acrylic resin, polystyrene resin, vinyl chloride resin, and polyester resin.

For the material of the substrate 3, in view of ensuring excellent stretching property and moisture permeability, preferably, polyurethane resin is used.

The substrate 3 has a thickness of, as a distance between the substrate lower face 12 and the substrate upper face 13 in a region other than the substrate groove 14, for example, 1 μm or more, preferably 5 μm or more, and for example, 300 μm or less, preferably 10 μm or less.

The wire layer 4 is embedded in the substrate groove 14. To be specific, the wire layer 4 is embedded in the upper portion of the substrate 3 so as to be exposed from the substrate upper face 13 of the substrate 3. The wire layer 4 has an upper face and a lower face disposed in spaced apart relation from each other, and side faces connecting their peripheral end edges. The entire lower face and the entire side face are in contact with the substrate 3. The upper face is exposed from the substrate upper face 13 (excluding substrate groove 14). The upper face of the wire layer 4 forms, along with the substrate upper face 13, upper face of the biosensor laminate 1.

As shown in FIG. 1, the wire layer 4 has a wire pattern connecting the connecter 6, electronic component 31 (described later), and battery 32 (described later). To be specific, the wire layer 4 independently includes a first wire pattern 41 and a second wire pattern 42.

The first wire pattern 41 is disposed at longitudinal one side of the substrate 3. The first wire pattern 41 includes a first wire 16A, and a first terminal 17A and a second terminal 17B continuous therefrom.

The first wire pattern 41 has a substantially letter T-shape in plan view. To be specific, the first wire 16A of the first wire pattern 41 extends from (connecter 6 positioned at) the longitudinal one end portion of the substrate 3 toward longitudinal other side, splits at the longitudinal center portion of the substrate 3, and extends toward transverse both outsides. The first wire 16A can have a wave shape, for improvement in stretching property of the biosensor laminate 1.

The first terminal 17A and the second terminal 17B each is disposed at transverse both end portions in longitudinal center portion of the substrate 3. The first terminal 17A and the second terminal 17B each has a substantially rectangular shape in plan view (land shape). The first terminal 17A and the second terminal 17B each is continuous with both end portions of the first wire 16A extending in transverse both outsides at a longitudinal center portion of the substrate 3.

The second wire pattern 42 is provided in spaced apart relation at longitudinal other side of the first wire pattern 41. The second wire pattern 42 includes a second wire 16B and a third terminal 17C and a fourth terminal 17D continuous therefrom.

The second wire pattern 42 has a substantially letter T-shape in plan view. To be specific, the second wire 16B of the second wire pattern 42 extends from (connecter 6 positioned at) the longitudinal other end portion of the substrate 3 toward longitudinal one side, splits at the longitudinal center portion of the substrate 3, and extends toward transverse both outsides. The second wire 16B can have a wave shape for improvement in stretching property of the biosensor laminate 1.

The third terminal 17C and the fourth terminal 17D each is disposed at transverse both end portions in longitudinal center portion of the substrate 3. The third terminal 17C and the fourth terminal 17D each has a substantially rectangular shape in plan view (land shape). The third terminal 17C and the fourth terminal 17D each is continuous with both end portions of the second wire 16B extending in transverse both outsides at a longitudinal center portion of the substrate 3.

For the material of the wire layer 4, for example, conductors such as copper, nickel, gold, and alloys thereof are used, and preferably, copper is used.

The wire layer 4 has a thickness of, for example, 0.1 μm or more, preferably 1 μm or more, and for example, 100 μm or less, preferably 10 μm or less.

As shown in FIG. 2A, the probe 5 is an electrode that allows sensing of electric signals, temperatures, vibrations, sweat, and metabolite from a living body, when the pressure-sensitive adhesive layer 2 is attached to the surface of the living body by making contact with the surface of the living body. In this embodiment, the probe 5 has a thin layer shape, and is disposed on the pressure-sensitive adhesive layer 2 so that at inside the adhesion opening 11, the probe lower face 20 as one face is exposed and the probe upper face 21 as an example of the other face is embedded in the pressure-sensitive adhesive layer 2. To be specific, the probe 5 is embedded in the adhesion groove 10 of the pressure-sensitive adhesive layer 2 at the inside of the adhesion opening 11.

The probe 5 has an exposure region 57, at which the pressure-sensitive adhesive layer 2 is exposed, to be described later. In this embodiment, the exposure region 57 includes a plurality of holes 52 disposed in spaced apart relation, and the probe 5 has a substantially mesh shape. The probe 5 has a probe lower face 20, a probe upper face 21 disposed to face the upper side of the probe lower face 20 in spaced apart relation, and side faces connecting peripheral end edges of the probe lower face 20 and the probe upper face 21.

The probe lower face 20 is exposed from the adhesive lower face 9 of the pressure-sensitive adhesive layer 2. The probe lower face 20 is flush with the adhesive lower face 9. The probe lower face 20 forms the lower face of the biosensor laminate 1 along with the adhesive lower face 9. The probe upper face 21 and the side face are covered with the pressure-sensitive adhesive layer 2.

As shown in FIG. 5, of the side faces of the probe 5, the face positioned at the outermost side is an outer side face 22. The outer side face 22 forms a virtual circle passing through the outer side face 22 in plan view.

For the material of the probe 5, those materials given as examples of the wire layer 4 (To be specific, conductors) are used.

The external size of the probe 5 is set so that the virtual circle passing through the outer side face 22 overlaps with the inner periphery defining the adhesion opening 11 in plan view.

The probe 5 has a thickness of, for example, 0.1 μm or more, preferably 1 μm or more, for example, less than 100 μm, preferably 10 μm or less.

The connecter 6 is provided in correspondence with the substrate opening 15 and the adhesion opening 11, and has the same shape as these. The connecter 6 penetrates (pass through) the substrate 3 and the pressure-sensitive adhesive layer 2 in thickness direction (up-down direction), and the substrate opening 15 and the adhesion opening 11 are filled with the connecter 6. The connecter 6 has a no-end shape in plan view along the outer side face 22 of the probe 5. To be specific, the connecter 6 has a substantially cylindrical shape with its axis line extending in thickness direction (along virtual circle passing through the outer side face 22).

As shown in FIG. 2A, the inner side face of the connecter 6 is in contact with the outer side face 22 of the probe 5. The connecter 6 is allowed to adhere to the pressure-sensitive adhesive layer 2 outside the adhesion opening 11 and the pressure-sensitive adhesive layer 2 inside the adhesion opening 11 by pressure-sensitive adhesion.

The upper face of the connecter 6 is flush with the substrate upper face 13. The lower face of the connecter 6 is flush with the adhesive lower face 9.

As shown in FIG. 1, of the two connecters 6, the connecter 6 positioned at longitudinal one side is continuous with, at its upper end portion, longitudinal one end edge of the longitudinal one side of the first wire 16A. The connecter 6 positioned at longitudinal other side is continuous with, at its upper end portion, longitudinal other end edge of the second wire 16B positioned at longitudinal other side.

In this manner, the connecter 6 electrically connects the wire layer 4 with the probe 5.

For the material of the connecter 6, for example, metal, electrical conductive resin (including electrical conductive polymer) are used, and preferably, electrical conductive resin is used.

The thickness of the connecter 6 (up-down direction length) is the same as a total thickness of the substrate 3 and the pressure-sensitive adhesive layer 2. The radial direction length of the connecter 6 (half the value deducting internal diameter from external diameter) is, for example, 1 μm or more, preferably 100 μm or more, and for example, 1000 μm or less, preferably 500 μm or less.

2. Description of Probe

Next, the probe 5 is described in detail with reference to FIG. 1.

As shown in FIG. 1, the probe 5 includes an exposure region 57 including a plurality of holes 52 disposed in spaced apart relation, and a bar portion 53 that defines the plurality of holes 52. At the bar portion 53, line-shaped bars are disposed to form a mesh.

In this embodiment, the bar portion 53 has a lattice shape, and integrally includes a plurality of first bar portions 54 and a plurality of second bar portions 55.

Each of the plurality of first bar portion 54 has a substantially rod shape extending in the entire longitudinal direction of the probe 5. The plurality of first bar portions 54 are disposed so as to be parallel to each other with a space provided therebetween in transverse direction. That is, the plurality of first bar portion 54 extend in a direction orthogonal to thickness direction of the pressure-sensitive adhesive layer 2 so as to be parallel to each other with a space provided therebetween.

The plurality of second bar portions 55 bridge the first bar portions 54 that are adjacent to each other out of the plurality of first bar portions 54. The plurality of second bar portions 55 each has a substantially rod shape extending in the entire transverse direction of the probe 5, and is orthogonal to (crossing) the plurality of first bar portions 54. The plurality of first bar portions 54 are continuous with the plurality of second bar portions 55 at portions where they are orthogonal to (crossing) each other.

The plurality of second bar portions 55 are disposed parallel to each other with a space provided therebetween in longitudinal direction. That is, the plurality of second bar portions 55 are parallel to each other with a space provided therebetween, and extend in transverse direction (second direction) orthogonal to both directions of the thickness direction and longitudinal direction (first direction) of the pressure-sensitive adhesive layer 2 so as to be orthogonal to (crossing) the plurality of first bar portions 54.

The size of the first bar portion 54 in the transverse direction (width of the first bar portion 54) and the size of the second bar portion 55 in the longitudinal direction (width of the second bar portion 55) are, for example, 10 μm or more, preferably 20 μm or more, more preferably 50 μm or more, and for example, 500 μm or less, preferably 300 μm or less, more preferably 100 μm or less.

The size of the first bar portion 54 in the transverse direction and the size of the second bar portion 55 in the longitudinal direction are preferably the same.

The exposure region 57 is a portion where the adhesive lower face 9 is exposed in the region (ref: description on the area of the probe 5) surrounded by the phantom line to be described later, and includes the plurality of holes 52.

The plurality of holes 52 give flexibility to the probe 5 so that the probe 5 can conform to subtle bumps and dips of the surface of the living body. The plurality of holes 52 are defined by the bar portion 53, and are disposed to be spaced apart from each other. The plurality of holes 52 include columns of the plurality of holes 52 that are arranged in spaced apart relation in longitudinal direction (second bar portion 55), and the plurality of columns are disposed in spaced apart relation in transverse direction (first bar portion 54).

The plurality of holes 52 allow the adhesive lower face 9 of the pressure-sensitive adhesive layer 2 to exposed from the lower side. The plurality of holes 52 are defined as spaces that are surrounded by the first bar portions 54 that are adjacent to each other out of the plurality of first bar portions 54 and the second bar portions 55 that cross these first bar portions 54 and are adjacent to each other. The holes 52 penetrate the probe 5 in thickness direction.

In this embodiment, the hole 52 has a rectangular shape in plan view, to be more specific, a square shape in plan view. The hole 52 is filled with the pressure-sensitive adhesive layer 2.

The size of the hole 52 in the longitudinal direction, and the size of the hole 52 in the transverse direction are, for example, 50 μm or more, preferably 200 μm or more, more preferably 300 μm or more, particularly preferably 400 μm or more, and for example, 1000 μm or less, preferably 900 μm or less.

The size of the first bar portion 54 in the transverse direction: the size of the hole 52 in the transverse direction is, for example, 5:95 to 50:50, and preferably 5:95 to 40:60, more preferably 5:95 to 20:80. The size of the second bar portion 55 in the longitudinal direction: the size of the hole 52 in the longitudinal direction is, for example, 5:95 to 50:50, and preferably 5:95 to 40:60, more preferably 5:95 to 20:80.

When the size of the first bar portion 54 in the transverse direction: the size of the hole 52 in the transverse direction, and the size of the second bar portion 55 in the longitudinal direction: the size of the hole 52 in the longitudinal direction are within the above-described range, the ratio of the area of the bar portion 53 to the area of the hole 52 can be ensured in good balance, and the probe 5 can conform to the subtle bumps and dips of the surface of the living body even more reliably.

The probe 5 has the hole 52 of a number of, for example, 50 or more, preferably 100 or more, and for example, 500,000 or less, preferably 50,000 or less.

The probe 5 has an area of, for example, 0.5 cm$^2$ or more, preferably 1 cm$^2$ or more, and for example, 10 cm$^2$ or less, preferably 5 cm$^2$ or less.

The area of the probe 5 is the area of the region surrounded by the phantom line connecting the outermost points in the cross section with a shortest distance, in the cross section cutting the probe 5 by a phantom plane orthogonal to the thickness direction of the probe 5.

Figure 7A:
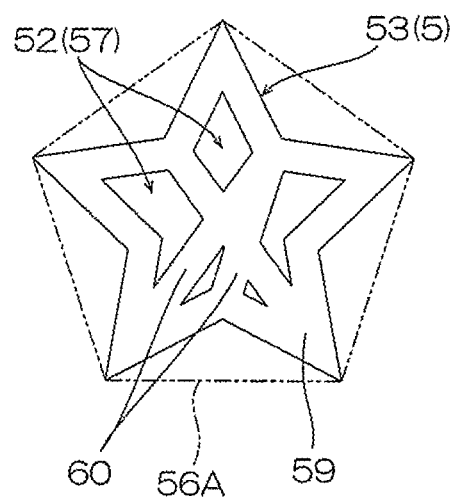
FIG. 7A and FIG. 7B are plan views of the probe in modified examples, FIG. 7A illustrating an embodiment in which the probe a star shaped frame, and FIG. 7B illustrating an embodiment in which the probe has a ring shaped frame.

For example, as shown in FIG. 7A, when the outmost portion in the cross section is the plurality of peaks, the area of the probe 5 is the area of the region surrounded by a phantom line 56A connecting the plurality of peaks by the shortest distance.

Figure 7B:
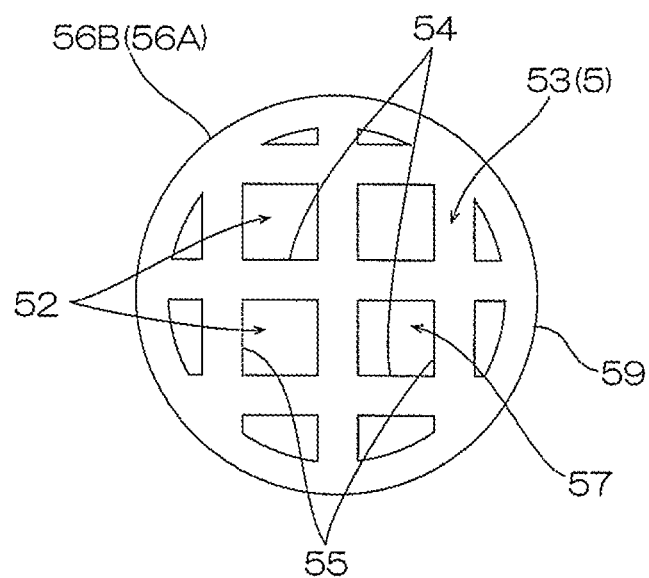

As shown in FIG. 7B, when the outmost portion in the cross section is all in lines, the phantom line 56A connecting the outermost portion in the cross section connected by the shortest distance coincide with the line 56B, and the area of the probe 5 is the area of the region surrounded by the line 56B.

Figure 9A:
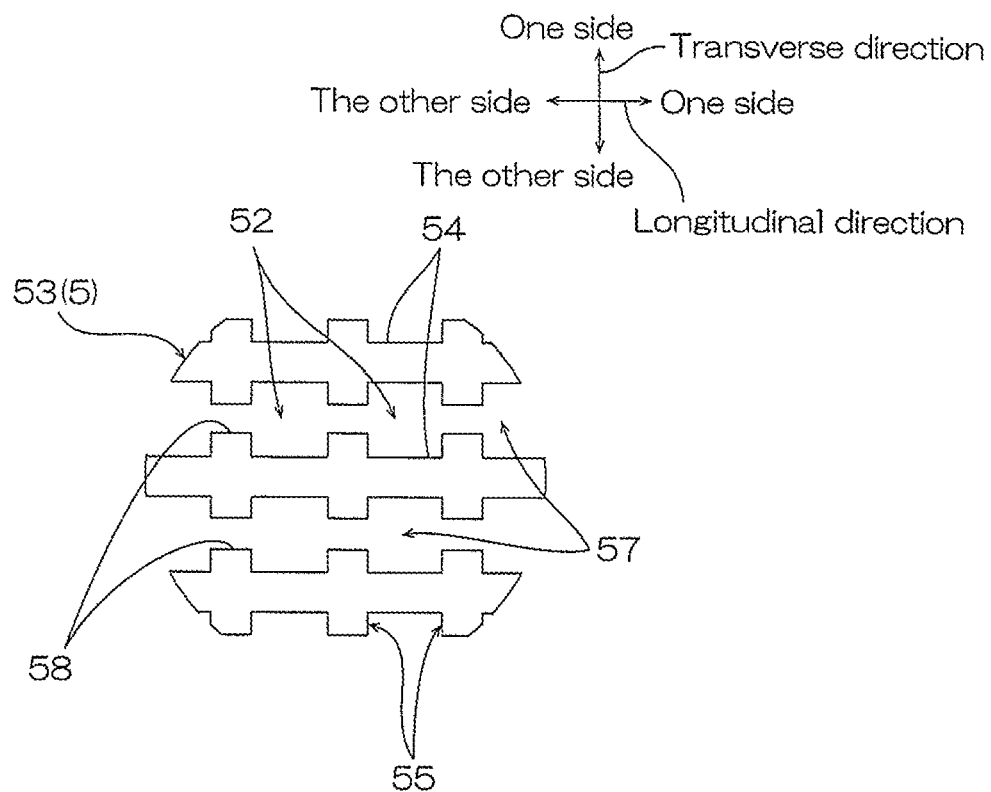
FIG. 9A and FIG. 9B are plan views of the probe in modified examples, FIG. 9A illustrating an embodiment in which the exposure region is formed with the plurality of holes communicating with each other, and FIG. 9B illustrating an embodiment in which the exposure region has a substantially U-shaped groove in plan view.
Figure 9B:
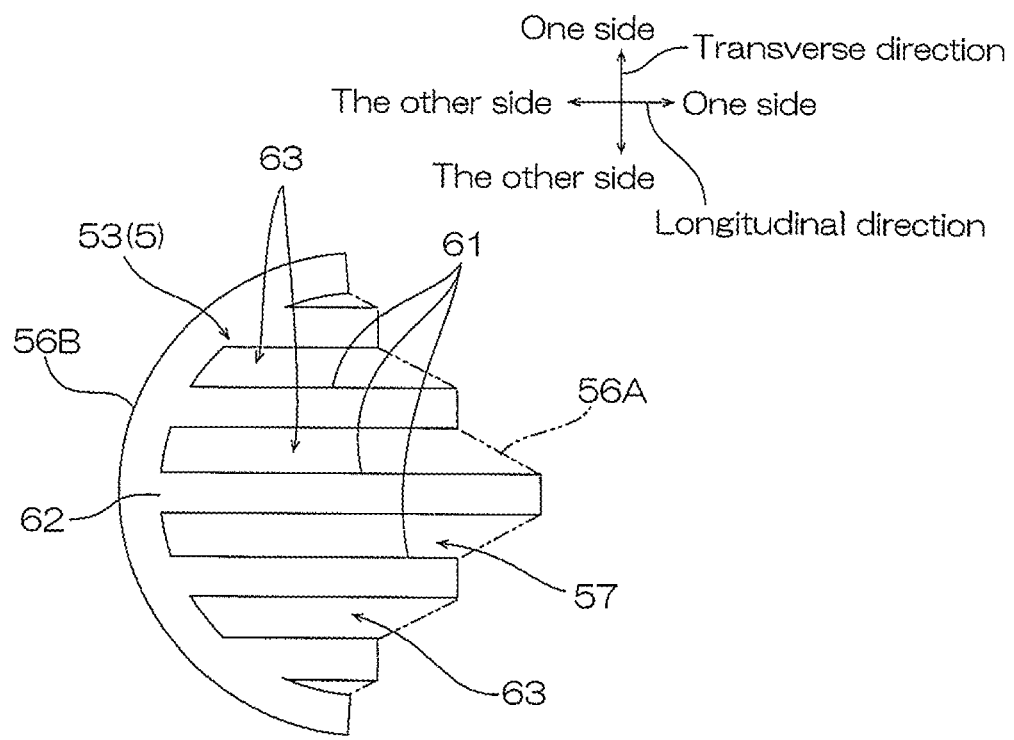

As shown in FIG. 9B, when the outermost portion in the cross section includes a plurality of peaks and lines, the area of the probe 5 is the area of the region surrounded by the phantom line 56A connecting the plurality of peaks by the shortest distance and line 56B.

A total of the area of the exposure region 57 (including the plurality of holes 52) relative to the area of the probe 5 is, for example, 50% or more, preferably 80% or more, and for example, 95% or less.

When the total of the area of the exposure region 57 relative to the area of the probe 5 is the above-described lower limit or more, the area of the holes 52 that allows moisture to pass through can be reliably and sufficiently ensured, and when the biosensor laminate 1 is attached to a living body, burden to the living body can be suppressed. When the total of the area of the exposure region 57 relative to the area of the probe 5 is the above-described upper limit or less, signal reception performance of the probe 5 can be sufficiently ensured.

3. Method for Producing Biosensor Laminate

Next, the method for producing a biosensor laminate 1 is described with reference to FIG. 3A to FIG. 5.

As shown in FIG. 3A to FIG. 3C, in this method, for example, first, a laminate 28 and a probe member 18 are separately prepared.

The laminate 28 includes a pressure-sensitive adhesive layer 2, a substrate 3 disposed on the upper face of the pressure-sensitive adhesive layer 2, and a wire layer 4 disposed on the substrate 3.

The pressure-sensitive adhesive layer 2, substrate 3, and wire layer 4 of the laminate 28 have the same configuration as those of the above-described pressure-sensitive adhesive layer 2, substrate 3, and wire layer 4, respectively.

To prepare the laminate 28, for example, after preparing the substrate 3 on which the wire layer 4 is disposed, the pressure-sensitive adhesive layer 2 is disposed on the substrate lower face 12 of the substrate 3.

The substrate 3 on which the wire layer 4 is disposed is prepared by embedding the wire layer 4 on the substrate groove 14 by the method described in, for example, Japanese Unexamined Patent Publication No. 2017-22236, and Japanese Unexamined Patent Publication No. 2017-22237.

To dispose the pressure-sensitive adhesive layer 2 on the substrate lower face 12, for example, first, an application liquid containing the materials for the pressure-sensitive adhesive layer 2 is prepared, and then the application liquid is applied on the upper face of the first release sheet 19, and thereafter, they are dried by heating. In this manner, the pressure-sensitive adhesive layer 2 is disposed on the upper face of the first release sheet 19. The first release sheet 19 has, for example, a substantially flat plate shape extending in longitudinal direction.

For the material of the first release sheet 19, for example, resin such as polyethylene terephthalate is used.

Thereafter, the pressure-sensitive adhesive layer 2 and the substrate 3 are bonded by, for example, a laminator. To be specific, the adhesive upper face 8 of the pressure-sensitive adhesive layer 2 is brought into contact with the substrate lower face 12 of the substrate 3.

At this point, the substrate 3 or the pressure-sensitive adhesive layer 2 has no substrate opening 15 or adhesion opening 11.

In this manner, a laminate 28 supported by the first release sheet 19 is prepared.

As shown in FIG. 3C and FIG. 5, a probe member 18 is prepared.

The probe member 18 includes a pressure-sensitive adhesive layer 2, a substrate 3 disposed on the upper face of the pressure-sensitive adhesive layer 2, and a thin-layer probe 5 disposed on the pressure-sensitive adhesive layer 2 so that the probe lower face 20 is exposed and the probe upper face 21 is embedded in the pressure-sensitive adhesive layer 2.

The pressure-sensitive adhesive layer 2, substrate 3, and probe 5 of the probe member 18 have the same configuration as those of the above-described pressure-sensitive adhesive layer 2, substrate 3, and probe 5, respectively.

Figure 4:
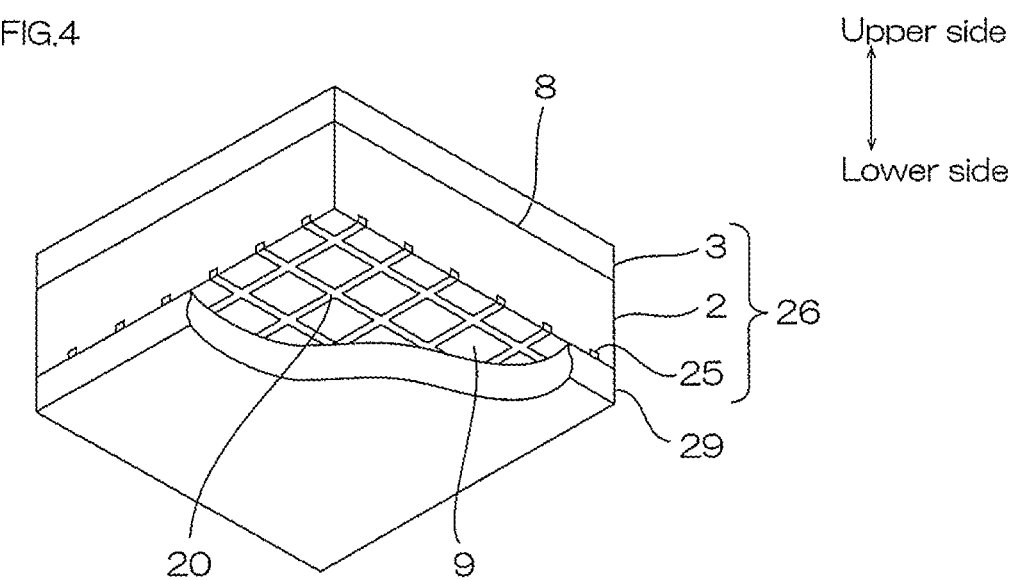
FIG. 4 shows a perspective view of a probe-containing sheet seen from the bottom, with a partially cut out second release sheet.

As shown in FIG. 4, to prepare the probe member 18, first, the probe-containing sheet 26 is prepared.

The probe-containing sheet 26 includes a pressure-sensitive adhesive layer 2, a probe pattern 25 embedded in the pressure-sensitive adhesive layer 2, and a substrate 3 disposed on the adhesive upper face 8 of the pressure-sensitive adhesive layer 2.

The probe pattern 25 has the same pattern as that of the probe 5, and the material of the probe pattern 25 is the same as the material of the probe 5. The probe pattern 25 has a flat area larger than the virtual circle passing through the outer side face 22 of the probe 5.

The probe-containing sheet 26 is prepared, for example, by the method described in Japanese Unexamined Patent Publication No. 2017-22236 and Japanese Unexamined Patent Publication No. 2017-22237.

Although not shown, to be specific, after forming a seed layer composed of copper on the upper face of a release layer composed of stainless steel, a photoresist is laminated on the entire upper face of the seed layer. Then, the photoresist is exposed to light and developed, thereby forming the photoresist into a reverse pattern of the probe pattern 25. Then, after the probe pattern 25 is formed on the upper face of the seed layer by electrolytic plating, the photoresist is removed. Thereafter, an application liquid containing the material of the pressure-sensitive adhesive layer 2 is applied to cover the probe pattern 25, and cured to form the pressure-sensitive adhesive layer 2. Then, the substrate 3 is bonded to the upper face of the pressure-sensitive adhesive layer 2 by, for example, a laminator. Then, the release layer is removed from the lower face of the seed layer, and then the seed layer is removed. Thereafter, as necessary, the second release sheet 29 is bonded to the lower face of the pressure-sensitive adhesive layer 2. The second release sheet 29 has the same configuration as that of the above-described first release sheet 19.

In this manner, the probe-containing sheet 26 is prepared.

As shown in FIG. 5, then, a cutting line 27 is formed on the probe pattern 25, pressure-sensitive adhesive layer 2, and substrate 3 into a generally circular shape in plan view. The cutting line 27 is formed, for example, by punching. The cutting line 27 divides the probe pattern 25, pressure-sensitive adhesive layer 2, and substrate 3 into inner portions and outer portions, but the cutting line 27 is not formed on the second release sheet 29. The size of the cutting line 27 is the same as the internal diameter of the adhesion opening 11 and substrate opening 15. That is, the cutting line 27 coincides with the virtual circle passing through the outer side face 22.

By forming the cutting line 27, the probe member 18 is formed.

In the probe member 18, the outer side face 22 of the probe 5 is flush with the outer side face of the pressure-sensitive adhesive layer 2. In the probe member 18, the outer side face 22 is exposed to the outside in radial direction from the outer side face of the pressure-sensitive adhesive layer 2.

Then, as shown in the arrow in FIG. 5, the probe member 18 is pulled out from the second release sheet 29. To be specific, the adhesive lower face 9 and probe lower face 20 of the probe member 18 are released from the second release sheet 29.

In the above-described manner, the probe member 18 is prepared.

The probe member 18 has a thickness (up-down direction size) of, the thickness (up-down direction size) of the laminate 28 or more, and preferably, has the same thickness as that of the laminate 28.

Then, as shown in FIG. 3C, a through hole 23 is formed on the laminate 28.

The through hole 23 penetrates the laminate 28 in up-down direction. The through hole 23 is a hole having a generally circular shape in plan view (through opening) defined by an outer peripheral face defining the substrate opening 15 and an outer peripheral face defining the adhesion opening 11. The first wire 16A (or second wire 16B) of the wire layer 4 is facing the through hole 23. The through hole 23 is opened toward the upper side. Meanwhile, the lower end of the through hole 23 is closed by the first release sheet 19.

The internal diameter of the through hole 23 is larger than the outer shape of the probe member 18. The through hole 23 has a size that allows formation of a gap 100 between the inner face 23A of the through hole 23 and the peripheral face 18A of the probe member 18 when the probe member 18 is disposed in the through hole 23.

To form the through hole 23, the laminate 28 is subjected to, for example, punching or half etching.

Then, as shown in the arrow in FIG. 3C, the probe member 18 is embedded in the through hole 23 so as to form the gap 100.

The gap 100 is formed by positioning the pressure-sensitive adhesive layer 2, substrate 3, and probe 5 of the probe member 18, and the pressure-sensitive adhesive layer 2 and substrate 3 surrounding the through hole 23 in spaced apart relation in the radial direction of the probe member 18. The wire layer 4 (first wire 16A or second wire 16B) and the outer side face 22 of the probe 5 are facing the gap 100.

Thereafter, as shown in FIG. 3D, a connecter 6 that electrically connects the wire layer 4 with the probe 5 is formed at the gap 100.

When the material of the connecter 6 is electrically conductive resin composition, the electrically conductive resin composition is injected (or applied) to the gap 100. Thereafter, as necessary, the electrically conductive resin composition is heated and cured.

In this manner, the biosensor laminate 1 is produced.

The biosensor laminate 1 includes the pressure-sensitive adhesive layer 2, substrate 3, wire layer 4, probe 5, connecter 6, and first release sheet 19, and preferably, the biosensor laminate 1 consist of these. As shown in FIG. 2A, the biosensor laminate 1 can consists of the pressure-sensitive adhesive layer 2, substrate 3, wire layer 4, probe 5, and connecter 6, without including the first release sheet 19.

The biosensor laminate 1 is distributed singly, and is an industrially applicable device. To be specific, the biosensor laminate 1 can be distributed singly, separately from the electronic component 31 and battery 32 (ref: phantom line in FIG. 1) to be described later. That is, the biosensor laminate 1 is not mounted with the electronic component 31 and battery 32, and is a component for producing a wearable electrocardiograph 30.

Next, description is given below of a method for producing a wearable electrocardiograph 30 as an example of the biosensor using the biosensor laminate 1, and a method of using the wearable electrocardiograph 30.

As shown in FIG. 1 and FIG. 2A, to produce the wearable electrocardiograph 30, for example, first, the biosensor laminate 1, electronic component 31, and battery 32 are prepared.

Examples of the electronic component 31 include an analog front-end, microcomputer, and memory for processing and storing electric signals from a living body obtained by the probe 5, and a communication IC and transmitter for converting electric signals to electro-magnetic waves and wirelessly transmitting them to an external receiver. The electronic component 31 can have some or all of these components. The electronic component 31 has two terminals or two or more terminals (not shown) provided at its lower face.

The battery 32 has two terminals (not shown) provided at its lower face.

Then, the two terminals of the electronic component 31 are electrically connected with the first terminal 17A and third terminal 17C. The two terminals of the battery 32 are electrically connected with the second terminal 17B and fourth terminal 17D.

In this manner, the wearable electrocardiograph 30 including the biosensor laminate 1, the electronic component 31 and the battery 32 mounted on the biosensor laminate 1 is produced.

To use the wearable electrocardiograph 30, first, the first release sheet 19 (ref: arrows and phantom line in FIG. 3D) is released from the pressure-sensitive adhesive layer 2 and probe 5.

As shown in the phantom line in FIG. 2A, then, the adhesive lower face 9 of the pressure-sensitive adhesive layer 2 is allowed to contact, for example, a skin 33 of a human body. To be specific, the pressure-sensitive adhesive layer 2 is allowed to pressure-sensitively adhere to a surface of the skin 33.

Then, the probe lower face 20 of the probe 5 makes contact with the surface of the skin 33, by allowing the adhesive lower face 9 to pressure-sensitively adhere (attaching) to the skin 33. At this time, the probe 5 bends so as to fit the skin 33 based on the plurality of holes 52, and conforms to subtle bumps and dips of the skin 33.

Then, the probe 5 senses cardiac action potential as electric signals, and the electric signals sensed at the probe 5 are inputted to the electronic component 31 through the connecter 6 and wire layer 4. The electronic component 31 processes the electric signal based on the electric power supplied from the battery 32, and store that information. Furthermore, as necessary, the electric signals are converted to electro-magnetic waves, and they are wirelessly transmitted to an external receiver.

In the biosensor laminate 1, as shown in FIG. 2A, the probe 5 has an exposure region 57 including a plurality of holes 52 disposed in spaced apart relation.

Therefore, when the pressure-sensitive adhesive layer 2 is attached to the skin 33 and the probe lower face 20 of the probe 5 is allowed to contact the surface of the skin 33, the exposure region 57 (the plurality of holes 52) allows the probe 5 to bend so as to fit the surface of the skin 33, and the probe 5 can conform to subtle bumps and dips of the surface of the skin 33.

As a result, biosignal sensing precision can be improved in the wearable electrocardiograph 30 including the biosensor laminate 1.

The probe 5 has a thin layer shape. Therefore, user's discomfort in wearing can be decreased when the biosensor laminate 1 is attached to the surface of the living body.

The plurality of holes 52 are defined by the bar portion 53. Therefore, while arranging the plurality of holes 52 regularly, flexibility can be given to the probe 5. As a result, the probe 5 can reliably conform to subtle bumps and dips of the surface of the living body.

The bar portion 53 has a lattice shape. Therefore, the plurality of holes 52 can be disposed homogenously in good balance in the entire probe 5. As a result, the entire probe 5 can reliably conform to subtle bumps and dips of the surface of the living body.

The plurality of holes 52 are defined by a plurality of first bar portions 54 that are parallel to each other with a space provided therebetween, and a plurality of second bar portions 55 that bridge the first bar portions 54 that are adjacent to each other. Therefore, the second bar portion 55 allows rigidity to be kept while flexibility can be given to the probe 5.

The size of the first bar portion 54 in the second direction: the size of the hole 52 in the second direction is within the above-described range, and the size of the second bar portion 55 in the first direction: the size of the hole 52 in the first direction is within the above-described range. Therefore, the ratio of the area of the bar portion 53 to the area of the hole 52 can be kept in good balance, and the probe 5 can reliably conform to subtle bumps and dips of the surface of the skin 33 even more.

The size of the first bar portion 54 in the transverse direction and the size of the second bar portion 55 in the longitudinal direction are within the above-described range, and the size of the hole 52 in the longitudinal direction and the size of the hole 52 in the transverse direction are within the above-described range. Therefore, the ratio of the area of the bar portion 53 to the area of the holes 52 can be reliably ensured even more in good balance.

Modified Example

In the modified examples below, the members and steps corresponding to those described in the embodiment above are designated by the same reference numerals, and detailed descriptions thereof are omitted. These modified examples can be suitably combined. Furthermore, the modified examples have the same operations and effects as those in the embodiment unless otherwise noted.

As shown in FIGS. 1 and 5, in the embodiment, the phantom line passing through the outer side face 22 is circular, but the shape is not particularly limited, and for example, although not shown, it can be rectangular.

In the embodiment, in the probe 5, the plurality of holes 52 are defined by the bar portions 53, but the probe 5 does not have to include the bar portions 53 as long as the plurality of holes 52 are included.

Figure 6A:
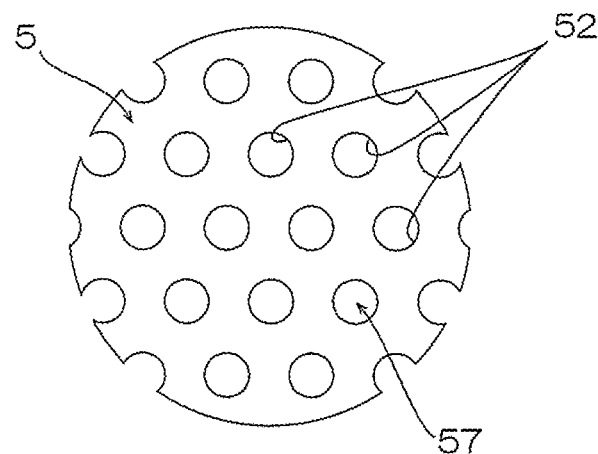
FIG. 6A to FIG. 6C are plan views of the probe in a modified example, FIG. 6A illustrating an embodiment in which the plurality of holes have a circular shape, FIG. 6B illustrating an embodiment in which the bar portion has a honeycomb shape, and FIG. 6C illustrating an embodiment in which the bar portion has a staggered shape.

For example, as shown in FIG. 6A, the platy probe 5 can include the plurality of holes 52 formed therein.

The shape of the plurality of holes 52 is not particularly limited, and for example, it can have a generally circular shape in plan view.

In the embodiment, the bar portion 53 has a lattice shape, but the shape of the bar portion 53 is not particularly limited. For example, the bar portion 53 can have a honeycomb shape, as shown in FIG. 6B, or a staggered shape, as shown in FIG. 6C.

Figure 6B:
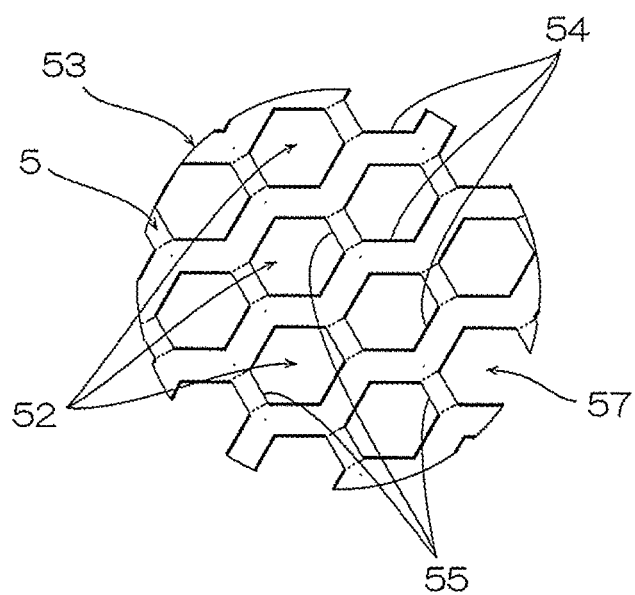

As shown in FIG. 6B, when the bar portion 53 has a honeycomb shape, each of the plurality of first bar portions 54 extends in longitudinal direction so as to form stepped stairs, and the plurality of first bar portions 54 are arranged in parallel to each other with a space provided therebetween in transverse direction. The plurality of second bar portions 55 bridge the first bar portions 54 that are adjacent to each other, out of the plurality of first bar portions 54. In FIG. 6B, for convenience, the plurality of first bar portions 54 are shown in bold lines. The hole 52 has a hexagonal shape in plan view, defined by the plurality of first bar portions 54 and the plurality of second bar portions 55.

Figure 6C:
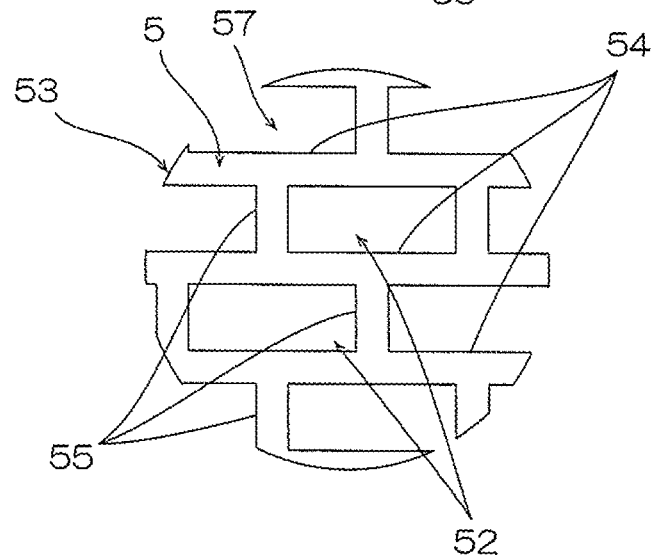

As shown in FIG. 6C, when the bar portion 53 has a staggered shape, the first bar portion 54 extends linearly in longitudinal direction, and the plurality of first bar portions 54 are disposed in parallel to each other with a space provided therebetween in transverse direction. The plurality of second bar portions 55 bridge the first bar portions 54 that are adjacent to each other at different positions in longitudinal direction so as not to be continuous in transverse direction, out of the plurality of first bar portions 54. The hole 52 has a substantially rectangular shape in plan view, defined by the first bar portion 54 and the second bar portion 55.

The shape of the probe 5 is not particularly limited. For example, the probe 5 can have a star shape as shown in FIG. 7A. Such a bar portion 53 of the probe 5 includes a frame 59 having a hollow star shape (to be specific, pentagonal star), and a plurality of bridge portions 60 disposed in the frame 59. The bridge portion 60 has a substantially rod shape extending in the surface direction of the probe 5. The plurality of bridge portions 60 bridge the portions facing each other in the inner side face of the frame 59 so as to define the plurality of holes 52 in the frame 59.

The shape of the frame 59 is not particularly limited. For example, the bar portion 53 can include, as shown in FIG. 7B, a ring shaped frame 59, a plurality of first bar portions 54, and a plurality of second bar portions 55. The frame 59 encircles the plurality of first bar portions 54 and the plurality of second bar portions 55, and is continuous with their end portions.

Figure 8A:
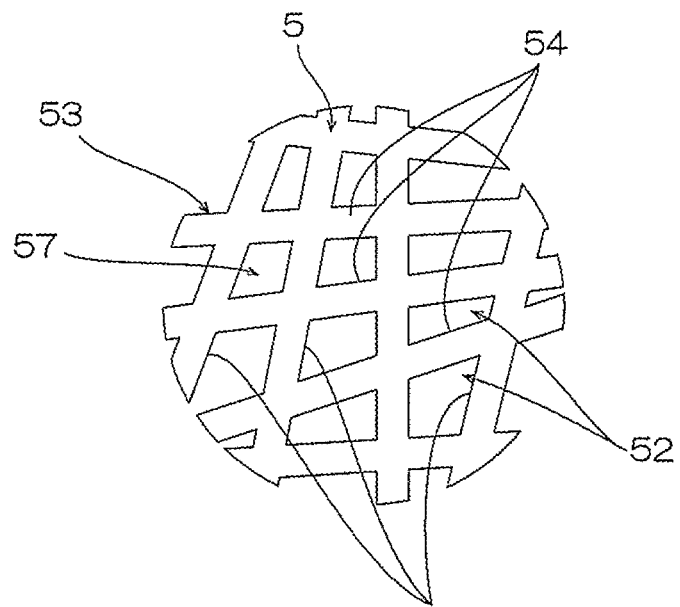
FIG. 8A to FIG. 8C are plan views of the probe in modified examples, FIG. 8A illustrating an embodiment in which the bar portion has a lattice shape including a plurality of first bar portions that are not parallel to each other and a plurality of second bar portions that are not parallel to each other, FIG. 8B illustrating an embodiment in which the bar portion has a lattice shape including a plurality of first bar portions and a plurality of second bar portions crossing at an angle of less than 90° C., and FIG. 8C illustrating an embodiment in which the bar portion has a lattice shape including a plurality of first bar portions and a plurality of second bar portions having a wave shape.

In the embodiment, the plurality of first bar portions 54 are disposed in parallel to each other, and the plurality of second bar portions 55 are disposed in parallel to each other, but it is not limited thereto. For example, as shown in FIG. 8A, the first bar portion 54 is tilted at an angle of less than ±45° relative to the longitudinal direction, and the plurality of first bar portions 54 are disposed in spaced apart relation in transverse direction so as not to be parallel to each other. The second bar portion 55 is tilted at an angle of less than ±45° relative to the transverse direction, and the plurality of second bar portions 55 are disposed in spaced apart relation in longitudinal direction so as not to be in parallel to each other.

Figure 8B:
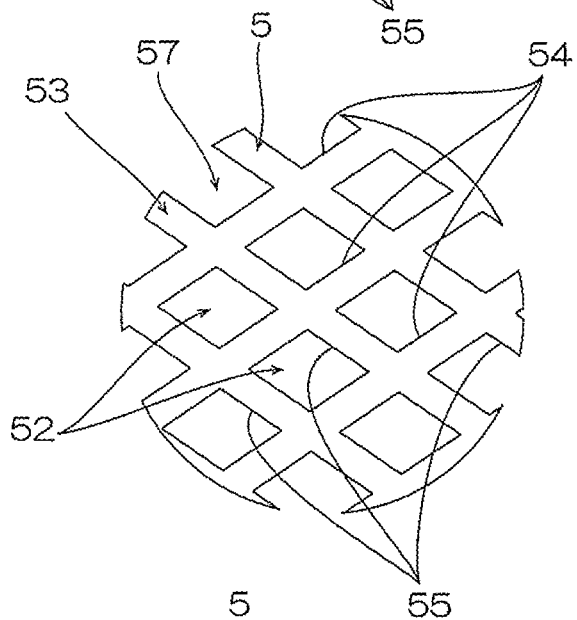

In the embodiment, the plurality of first bar portions 54 and plurality of second bar portions 55 are orthogonal, but as shown in FIG. 8B, the plurality of first bar portion 54 can cross the plurality of second bar portions 55 at an angle of less than 90° C. (or an angle of more than 90° C.). The hole 52 has a substantially rhomboid shape in plan view, defined by the plurality of first bar portions 54 and the plurality of second bar portions 55.

Figure 8C:
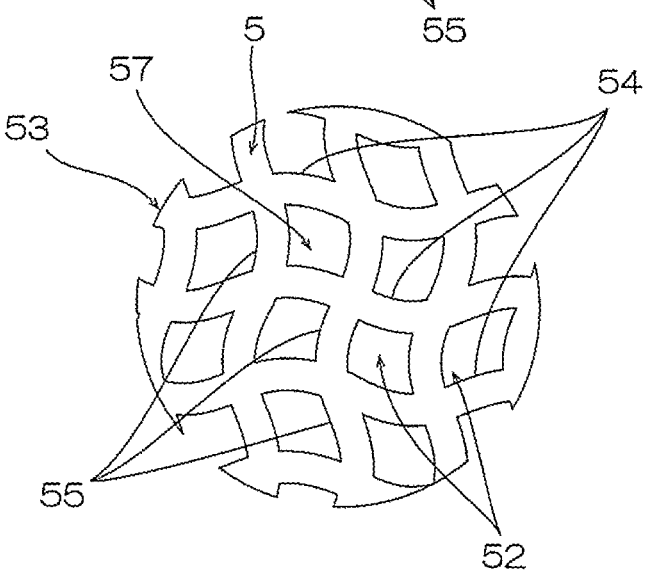

In the embodiment, the first bar portion 54 and the second bar portion 55 extend linearly, but their shapes are not particularly limited. As shown in FIG. 8C, the first bar portion 54 and the second bar portion 55 can have a wave shape. In the embodiments shown in FIG. 8A to FIG. 8C, the bar portion 53 has a lattice shape.

In the embodiment, the exposure region 57 includes the plurality of holes 52, but the exposure region 57 is not particularly limited, as long as it can allow the adhesive lower face 9 of the pressure-sensitive adhesive layer 2 to expose.

For example, as shown in FIG. 9A, the exposure region 57 can be formed by the plurality of holes 52 communicating each other. In this case, for example, the second bar portion 55 has cut out portions 58 that allow the holes 52 adjacent to each other in longitudinal direction to communicate. The cut out portion 58 is formed by cutting out a portion of the second bar portions 55. Although not shown, the first bar portions 54 can have cut out portions that allow the holes 52 adjacent to each other to communicate in transverse direction.

As shown in FIG. 9B, the exposure region 57 can include a groove 63 having a substantially U-shape in plan view and opened toward one side in a predetermined direction. In this case, the bar portion 53 includes a plurality of grooves 63, a plurality of first bar portions 61 extending in a predetermined direction, and second bar portions 62 connecting the other end portion of the plurality of first bar portions 61 in a predetermined direction.

To be specific, a plurality of first bar portions 61 extend in longitudinal direction to be parallel to each other with a space provided therebetween in transverse direction. The size of the first bar portion 61 in the longitudinal direction can be the same or different. In FIG. 9B, the size of the first bar portion 61 in the longitudinal direction is different from each other. The plurality of first bar portions 61 are disposed so that the longest first bar portion 61 out of the plurality of first bar portions 61 is disposed at a center in transverse direction and the length of the first bar portion 61 gradually shortens as it approaches the outside in transverse direction.

The second bar portion 62 connects the longitudinal other end portion of the plurality of first bar portions 61. The second bar portion 62 has a substantially arc shape in plan view, opening toward one side in longitudinal direction.

The groove 63 is defined as a space surrounded by the first bar portions 61 that are adjacent to each other out of the plurality of first bar portions 61, and the second bar portion 62 that connects these first bar portions 61. The groove 63 has a substantially U-shape in plan view opened toward one side in longitudinal direction.

Figure 10:
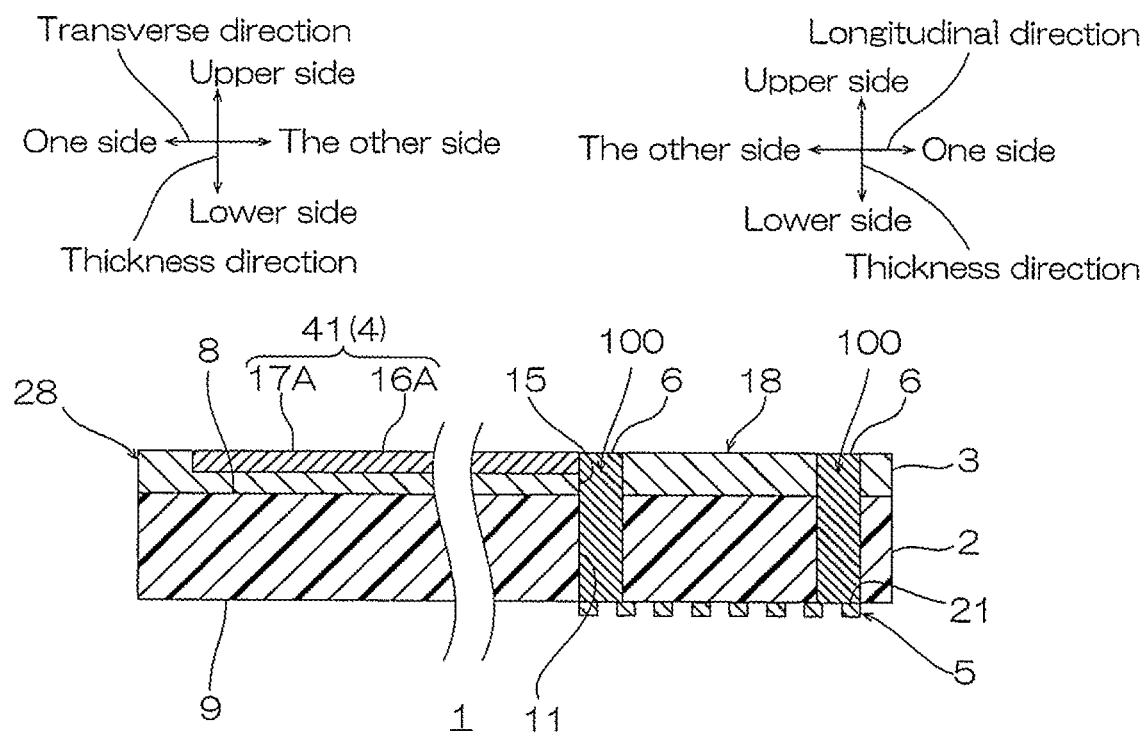
FIG. 10 is a cross sectional view of the biosensor laminate in a modified example (in which probe is disposed on adhesive lower face) of the embodiment.

In the embodiment, the probe 5 is embedded in the pressure-sensitive adhesive layer 2, as shown in FIG. 2A, but it is not particularly limited, as long as it is disposed on the pressure-sensitive adhesive layer 2. As shown in FIG. 10, for example, the probe 5 can be disposed on the adhesive lower face 9 of the pressure-sensitive adhesive layer 2. In this case, the probe upper face 21 of the probe 5 makes contact with the lower face of the connecter 6, so that the probe 5 and the connecter 6 are electrically connected.

In the embodiment, the biosensor laminate 1 is given as an example of the biosensor sheet of the present invention, but the biosensor sheet of the present invention includes a probe member 18 having a pressure-sensitive adhesive layer 2 and a probe 5, and a probe-containing sheet 26 having a pressure-sensitive adhesive layer 2 and a probe pattern 25 (an example of probe). The biosensor sheet of the present invention may not include the substrate 3 as long as the pressure-sensitive adhesive layer 2 and probe 5 are included.

In the embodiment, the wearable electrocardiograph 30 is given as an example of the biosensor, but for example, examples of the biosensors include devices that can sense biosignals and monitors conditions of a living body, and to be specific, a wearable electroencephalograph, wearable sphygmomanometer, wearable pulse meter, wearable electromyograph, wearable thermometer, and wearable accelerometer are included. These devices can be individual devices, or can be a device including the plurality of these devices.

The living body includes a human body and a living thing other than the human body, but preferably, the living body is a human body.

EXAMPLES

Hereinafter, the present invention is described in further detail with reference to Examples and Comparative Examples. However, the present invention is not limited to those described in Examples and Comparative Examples.

The specific numerical values of mixing ratio (content), physical property value, and parameter used in the description below can be replaced with the upper limit values (numerical values defined with "or less" or "below") or lower limit values (numerical values defined with "or more" or "more than") of the corresponding numerical values of mixing ratio (content), physical property value, and parameter described in "DESCRIPTION OF EMBODIMENTS" above.

Examples 1 to 6 and Comparative Example 1

1. Preparation of Laminate
(1) Preparation of Substrate and Wire Layer

A seed layer composed of copper was formed on the upper face of a stainless steel-made release layer by electrolytic copper plating, and then a dry film photoresist was laminated on the entire upper face of the seed layer. Then, the dry film photoresist was exposed to light and developed, thereby forming the dry film photoresist into an opposite pattern of the wire layer. Thereafter, the wire layer was formed on the upper face of the seed layer by electrolytic plating, and then the dry film photoresist was removed by a release solution.

Thereafter, an application liquid prepared as described below for a substrate was applied so as to cover the wire layer, and thereafter, it was dried at 120° C. for 5 minutes, thereby forming a substrate.

A polyether urethane solution (trade name [T-8180N], 20 mass % solution of polyether urethane (solvent=methyl ethyl ketone: dimethylformamide=1:1), manufactured by DIC Covestro Polymer Ltd.) and capric triglyceride were stirred and blended under normal temperature so that the mass ratio of the polyether urethane to capric triglyceride was 100/10, thereby preparing an application liquid for a substrate.

Then, the release layer was released from the lower face of the seed layer, and then the seed layer was removed by wet etching.

In this manner, a substrate on which the wire layer was disposed was prepared. The area of the substrate was 25 cm$^2$.

(2) Preparation of Pressure-Sensitive Adhesive Layer

Acrylic polymer was prepared from acrylic acid isononyl (iNA), acrylic acid methoxy ethyl (MEA), and acrylic acid (AA) in accordance with the description of Example 1 of Japanese Unexamined Patent Publication No. 2003-342541.

Then, 100 parts by mass of acrylic polymer, 60 parts by mass of capric triglyceride, and 0.01 parts by mass CORONATE® HL (trade name, polyfunctional isocyanate compound, manufactured by Nippon Polyurethane Industry Co., Ltd.) as a cross-linking agent were stirred and blended, thereby preparing an application liquid for a pressure-sensitive adhesive layer. Thereafter, the application liquid for a pressure-sensitive adhesive layer was applied on the surface of a PET film (first release sheet) with its surface treated for release, and thereafter, dried at 120° C. for 3 minutes, and further aged at 60° C. for 72 hours. In this manner, a pressure-sensitive adhesive layer supported by a release layer was prepared.

(3) Bonding of Substrate with Pressure-Sensitive Adhesive Layer

Thereafter, the pressure-sensitive adhesive layer was bonded to the lower face of the substrate by a vacuum laminator at 60° C.

In the above-described manner, a laminate supported by a PET film was prepared.

2. Preparation of Probe Member

The dry film photoresist on the seed layer was formed to be an opposite pattern of the probe pattern in the same manner as in the above-described preparation of the laminate. Thereafter, the probe pattern was formed on the upper face of the seed layer by electrolytic plating, and then the dry film photoresist was removed by a release solution.

The probe pattern had a lattice pattern in which a plurality of first bar portions and a plurality of second bar portions were orthogonal to each other. The plurality of holes had a square shape in plan view. The width L (width of first bar portion and second bar portion) of the bar portions, and the size (S) of a side of the hole are shown in Table 1. The probe pattern had a thickness of 2 μm. In Comparative Example 1, the probe pattern had a substantially flat plate shape, and did not have the plurality of holes.

Thereafter, the application liquid for the above-described pressure-sensitive adhesive layer was applied to cover the probe pattern, and thereafter, dried at 120° C. for 3 minutes, and further aged at 60° C. for 72 hours. In this manner, a pressure-sensitive adhesive layer on which the probe pattern was embedded was prepared.

Then, the above-described application liquid for a substrate was applied to the upper face of the pressure-sensitive adhesive layer, and then dried at 120° C. for 5 minutes. In this manner, the substrate was prepared.

The biosensor laminate was produced in the above manner.

Evaluation (Measurement of Resistance Value)

Two biosensor laminates of Examples were prepared.

Figure 11:
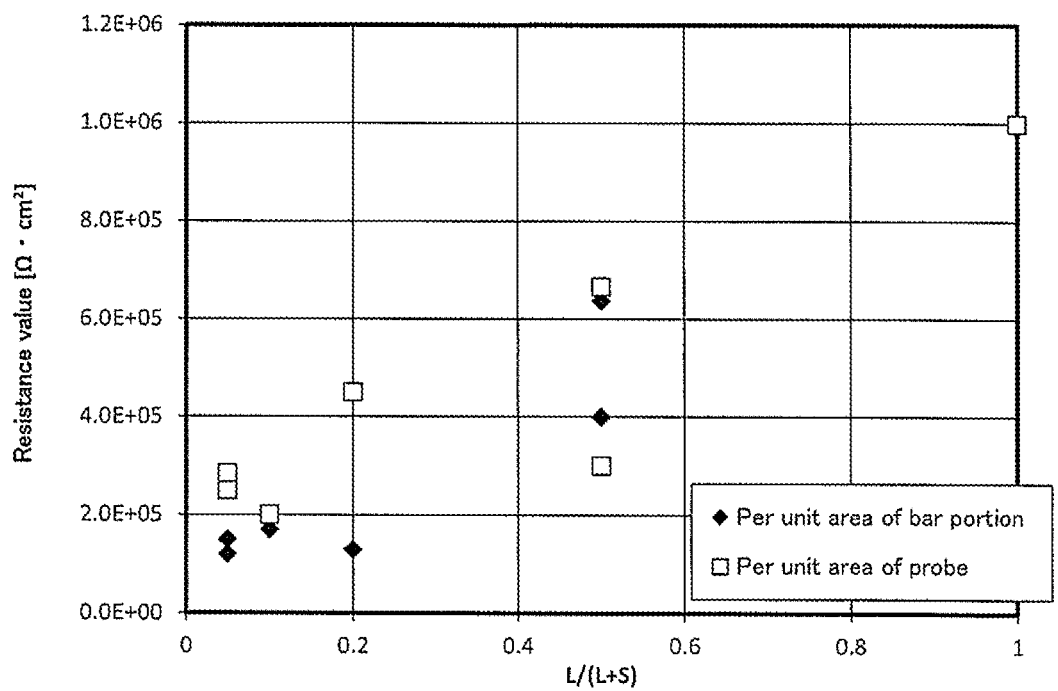
FIG. 11 is a graph illustrating the measurement results of the resistance in Examples and Comparative Examples.

Then, water was dropped to the lower face of the probe of the two biosensor laminates, and the two biosensor laminates were attached to a skin with an interval of 1 cm. Then, the wires of the two biosensor laminates were electrically connected to a digital multimeter (manufactured by ADC CORPORATION, R6552), and the resistance between the two probes with the skin interposed therebetween (including the skin resistance) was measured. The results are shown in Table 1 and FIG. 11.

TABLE 1

| No. | | Comp. Ex. 1 | Ex. 1 | Ex. 2 | Ex. 3 | Ex. 4 | Ex. 5 | Ex. 6 |
|---|---|---|---|---|---|---|---|---|
| Bar portion area | [cm$^2$] | 1 | 1 | 1 | 1 | 1 | 1 | 1 |
| Probe area | [cm$^2$] | 1 | 2 | 2 | 5 | 10 | 20 | 20 |
| Total hole area relative to probe area | [%] | 0 | 50 | 50 | 80 | 90 | 95 | 95 |
| Width of bar portion (L) | [μm] | 0 | 300 | 50 | 50 | 50 | 50 | 25 |
| Side of holes (S) | [μm] | — | 300 | 50 | 200 | 450 | 950 | 475 |
| L:S | [—] | — | 50:50 | 50:50 | 20:80 | 10:90 | 5:95 | 5:95 |
| Resistance value | Per unit area of bar portion [Ω · cm$^2$] | 9.90 × 10$^5$ | 4.00 × 10$^5$ | 6.37 × 10$^5$ | 1.30 × 10$^5$ | 1.70 × 10$^5$ | 1.50 × 10$^5$ | 1.20 × 10$^5$ |
| | Per unit area of probe [Ω · cm$^2$] | 9.99 × 10$^5$ | 3.00 × 10$^5$ | 6.66 × 10$^5$ | 4.50 × 10$^5$ | 2.00 × 10$^5$ | 2.50 × 10$^5$ | 2.85 × 10$^5$ |

Then, the release layer was released from the lower face of the seed layer, and then the seed layer was removed by wet etching. In this manner, a probe-containing sheet was prepared.

Thereafter, the probe-containing sheet was punched to form a cutting line having a generally circular shape in plan view. The formation of the cutting line formed the probe member.

Then, the probe member was separated from the probe-containing sheet, thereby preparing the probe member.

The thickness of the probe member was the same as that of the laminate.

3. Formation of Through Hole and Connecter

Then, through holes were formed on the laminate by half etching.

The internal diameter of the through hole was larger than the contour of the probe member, and the through hole had a size that allows a gap to be formed between the inner face of the through hole and the peripheral face of the probe member when the probe member is disposed in the through hole.

Then, the probe member was inserted to the through hole so as to form the above-described gap.

Thereafter, the electrical conductive resin composition was injected to the gap, and heated to be cured. In this manner, a connecter that electrically connects the wire layer with the probe was formed.

While the illustrative embodiments of the present invention are provided in the above description, such is for illustrative purpose only and it is not to be construed as limiting in any manner Modification and variation of the present invention that will be obvious to those skilled in the art is to be covered by the following claims.

INDUSTRIAL APPLICABILITY

The biosensor sheet of the present invention can be suitably used for various industrial products. For example, the biosensor sheet of the present invention is suitably used for a device that can sense biosignals and monitor the conditions of a living body: to be more specific, a wearable electrocardiograph, wearable electroencephalograph, wearable sphygmomanometer, wearable pulse meter, wearable electromyograph, wearable thermometer, and wearable accelerometer.

DESCRIPTION OF REFERENCE NUMERALS

1 biosensor laminate
2 pressure-sensitive adhesive layer
5 probe
52 hole
53 bar portion
54 first bar portion
55 second bar portion

The invention claimed is:

1. A biosensor sheet comprising:
a pressure-sensitive adhesive layer for attaching to a surface of a living body, and a probe disposed on the pressure-sensitive adhesive layer, wherein
the probe has a thin layer shape,
the probe is in contact with the pressure-sensitive adhesive layer,
the probe has an exposure region in which the pressure-sensitive adhesive layer is exposed,
a probe lower face of the probe is exposed from a lower face of the pressure-sensitive adhesive layer,
an area of the probe is an area of a region surrounded by a phantom line connecting outermost points in a cross section with a shortest distance, wherein the cross section is taken by cutting the probe by a phantom plane orthogonal to a thickness direction of the probe, and
a total of the area of the exposure region relative to the area of the probe is 50% or more and 95% or less.

2. The biosensor sheet according to claim 1, wherein the exposure region includes a plurality of holes disposed in spaced apart relation.

3. The biosensor sheet according to claim 2, wherein the probe includes a bar portion that defines the plurality of holes.

4. The biosensor sheet according to claim 3, wherein the bar portion has a lattice shape.

5. The biosensor sheet according to claim 3, wherein the bar portion comprises
a plurality of first bar portions extending in a direction orthogonal to a thickness direction of the pressure-sensitive adhesive layer so as to be parallel to each other with a space provided therebetween, and
a plurality of second bar portions that bridge adjacent first bar portions of the plurality of first bar portions.

6. The biosensor sheet according to claim 5, wherein
the plurality of first bar portions extend in a first direction orthogonal to the thickness direction,
the plurality of second bar portions extend in a second direction crossing both directions of the thickness direction and the first direction so as to be spaced apart from each other and to cross the plurality of first bar portions,
the ratio of the size of the first bar portion in the second direction: the size of the hole in the second direction is 5:95 to 50:50, and
the ratio of the size of the second bar portion in the first direction: the size of the hole in the first direction is 5:95 to 50:50.

7. The biosensor sheet according to claim 6, wherein
the size of the first bar portion in the second direction and the size of the second bar portion in the first direction are 10 µm or more and 500 µm or less, and
the size of the hole in the first direction and the size of the hole in the second direction are 50 µm or more and 1000 µm or less.

* * * * *